US007297522B2

(12) United States Patent
Cheung

(10) Patent No.: US 7,297,522 B2
(45) Date of Patent: *Nov. 20, 2007

(54) METHODS AND COMPOSITIONS FOR TREATING EPILEPSY

(75) Inventor: Ling Yuk Cheung, Hong Kong (HK)

(73) Assignee: Ultra Biotech Limited, Douglas (IM)

( * ) Notice: Subject to any disclaimer, the term of this patent is extended or adjusted under 35 U.S.C. 154(b) by 229 days.

This patent is subject to a terminal disclaimer.

(21) Appl. No.: 10/717,137

(22) Filed: Nov. 18, 2003

(65) Prior Publication Data
US 2005/0106171 A1 May 19, 2005

(51) Int. Cl.
C12N 1/14 (2006.01)
C12N 13/00 (2006.01)

(52) U.S. Cl. ............................. 435/173.1; 435/255.1; 435/255.2; 435/173.8

(58) Field of Classification Search .......... 424/195.16, 424/195, 160; 435/254.2, 254.21, 173.1, 435/255.1, 255.2, 173.8
See application file for complete search history.

(56) References Cited

U.S. PATENT DOCUMENTS

| | | |
|---|---|---|
| 2,107,830 A | 2/1938 | Liebesny et al. |
| 3,150,979 A | 9/1964 | Ensley |
| 3,711,392 A | 1/1973 | Metzger |
| 3,870,599 A | 3/1975 | Azarowicz |
| 3,923,279 A | 12/1975 | Gresley et al. |
| 3,939,279 A | 2/1976 | Kawano et al. |
| 3,968,254 A | 7/1976 | Rhodes et al. |
| 3,997,675 A | 12/1976 | Eichelburg |
| 4,041,182 A | 8/1977 | Erickson et al. |
| 4,081,367 A | 3/1978 | Hulls et al. .................. 210/610 |
| 4,118,512 A | 10/1978 | Eichelburg |
| 4,183,807 A | 1/1980 | Yoshizawa et al. .......... 210/611 |
| 4,211,645 A | 7/1980 | Zajic et al. .................. 210/611 |
| 4,348,483 A | 9/1982 | Skogerson |
| 4,559,305 A | 12/1985 | Zajic et al. .................. 435/243 |
| 4,816,158 A | 3/1989 | Shimura et al. ............. 210/610 |
| 5,047,250 A | 9/1991 | Prieels et al. |
| 5,075,008 A | 12/1991 | Chigusa et al. .............. 210/610 |
| 5,082,662 A | 1/1992 | Laurent et al. |
| 5,082,936 A | 1/1992 | Jamas et al. |
| 5,106,594 A | 4/1992 | Held et al. ................... 422/292 |
| 5,158,788 A | 10/1992 | Lavens et al. |
| 5,416,010 A | 5/1995 | Langenberg et al. ......... 435/468 |
| 5,476,787 A | 12/1995 | Yokoyama et al. ........ 435/262.5 |
| 5,504,079 A | 4/1996 | Jamas et al. |
| 5,567,314 A | 10/1996 | Chigusa et al. .............. 210/150 |
| 5,578,486 A | 11/1996 | Zhang ......................... 435/243 |
| 5,665,352 A | 9/1997 | Blehaut et al. |
| 5,707,524 A | 1/1998 | Potter ......................... 210/606 |
| 5,866,116 A | 2/1999 | Yaegaki |
| 5,879,928 A | 3/1999 | Dale et al. ................... 435/264 |
| 5,952,020 A | 9/1999 | Lizak |
| 5,981,219 A | 11/1999 | Flugge et al. |
| 6,036,854 A | 3/2000 | Potter ......................... 210/177 |
| 6,045,834 A | 4/2000 | Howes et al. |
| 6,143,731 A | 11/2000 | Jamas et al. |
| 6,159,510 A | 12/2000 | Lizak |
| 6,197,295 B1 | 3/2001 | Hsia et al. |
| 6,214,337 B1 | 4/2001 | Hayen et al. |
| 6,391,617 B1 | 5/2002 | Cheung ....................... 435/254 |
| 6,391,618 B1 | 5/2002 | Cheung ....................... 435/255 |
| 6,391,619 B1 | 5/2002 | Cheung ....................... 435/255 |
| 6,416,982 B1 | 7/2002 | Zhang |
| 6,416,983 B1 | 7/2002 | Cheung |
| 6,436,695 B1 | 8/2002 | Cheung ....................... 435/264 |
| 6,440,713 B1 | 8/2002 | Cheung ....................... 435/173 |
| 6,589,994 B1 * | 7/2003 | Artman et al. .............. 514/629 |
| 6,596,272 B2 | 7/2003 | Cheung |
| 6,596,273 B2 | 7/2003 | Cheung |
| 6,649,383 B1 | 11/2003 | Cheung .................... 435/173.1 |
| 6,660,508 B1 | 12/2003 | Cheung .................... 435/173.1 |
| 6,699,496 B1 | 3/2004 | Kojima et al. |
| 6,761,886 B2 | 7/2004 | Cheung |
| 6,800,466 B2 | 10/2004 | Cheung |
| 6,828,131 B2 | 12/2004 | Zhang |
| 6,828,132 B2 | 12/2004 | Cheung |

(Continued)

FOREIGN PATENT DOCUMENTS

CN 1110317 A 10/1995

(Continued)

OTHER PUBLICATIONS

Dutta et al. J. Microwave Power (1979), vol. 14, No. 3, pp. 275-280.*
"Saccharomyces cerevisiae Meyen ex Hansen Chinese Strain name" http://www.im/ac/cn/database/CCCCM/YEAST/y133.htm), Apr. 24, 1996.*
Agarwal N. et al., "Selection of *Saccharomyces cerevisiae* strains for use as a microbial feed additive," *Letters in Applied Microbiology*, 31:270-273 (2000).
Asami, K. et al., "Real-Time Monitoring of Yeast Cell Division by Dielectric Spectroscopy", *Biophysical Journal*, 76, pp. 3345-3348 (1999).
Balcer-Kubiczek, E.K. et al., "Expression Analysis of Human HL60 Cells Exposed to 60 Hz Square-or Sine-Wave Magnetic Fields", *Radiation Research*, 153, pp. 670-678 (2000).

(Continued)

Primary Examiner—Christopher R Tate
Assistant Examiner—Randall Winston
(74) Attorney, Agent, or Firm—Fish & Neave IP Group Ropes and Gray LLP

(57) ABSTRACT

Compositions comprising a plurality of yeast cells, wherein said plurality of yeast cells have been cultured in the presence of an alternating electric field having a specific frequency and a specific field strength for a period of time sufficient to increase the capability of said plurality of yeast cells to treat epilepsy. Also included are methods of making such compositions and methods of treating epilepsy.

7 Claims, 2 Drawing Sheets

U.S. PATENT DOCUMENTS

| | | |
|---|---|---|
| 2002/0099026 A1 | 7/2002 | Goodman et al. |
| 2002/0123127 A1 | 9/2002 | Cheung ........................ 435/254 |
| 2002/0123129 A1 | 9/2002 | Cheung ........................ 435/254 |
| 2002/0123130 A1 | 9/2002 | Cheung ........................ 435/262 |
| 2003/0230126 A1 | 12/2003 | Cheung |
| 2003/0230245 A1 | 12/2003 | Cheung |
| 2003/0232038 A1 | 12/2003 | Cheung |
| 2003/0232039 A1 | 12/2003 | Cheung |
| 2003/0232059 A1 | 12/2003 | Cheung |
| 2003/0235565 A1 | 12/2003 | Cheung |
| 2003/0235566 A1 | 12/2003 | Cheung |
| 2003/0235567 A1 | 12/2003 | Cheung |
| 2003/0235568 A1 | 12/2003 | Cheung |
| 2003/0235569 A1 | 12/2003 | Cheung |
| 2003/0235570 A1 | 12/2003 | Cheung |
| 2004/0001812 A1 | 1/2004 | Cheung |
| 2004/0001813 A1 | 1/2004 | Cheung |
| 2004/0001814 A1 | 1/2004 | Cheung |
| 2004/0001815 A1 | 1/2004 | Cheung ................... 424/93.51 |
| 2004/0001857 A1 | 1/2004 | Cheung ................. 424/195.16 |
| 2004/0001858 A1 | 1/2004 | Cheung ................. 424/195.16 |
| 2004/0001859 A1 | 1/2004 | Cheung ................. 424/195.16 |
| 2004/0001860 A1 | 1/2004 | Cheung ................. 424/195.16 |
| 2004/0001861 A1 | 1/2004 | Cheung ................. 424/195.16 |
| 2004/0005335 A1 | 1/2004 | Cheung |
| 2004/0005337 A1 | 1/2004 | Cheung ................. 424/195.16 |
| 2004/0005680 A1 | 1/2004 | Cheung |
| 2004/0168492 A1 | 9/2004 | Cheung |
| 2004/0253251 A1 | 12/2004 | Cheung |
| 2004/0253252 A1 | 12/2004 | Cheung |
| 2004/0253253 A1 | 12/2004 | Cheung |
| 2004/0253254 A1 | 12/2004 | Cheung |
| 2004/0253255 A1 | 12/2004 | Cheung |
| 2004/0253256 A1 | 12/2004 | Cheung |
| 2004/0253257 A1 | 12/2004 | Cheung |
| 2004/0253258 A1 | 12/2004 | Cheung |
| 2004/0253259 A1 | 12/2004 | Cheung |
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0253268 A1 | 12/2004 | Cheung |
| 2004/0265990 A1 | 12/2004 | Cheung |

FOREIGN PATENT DOCUMENTS

| | | |
|---|---|---|
| CN | 1207873 | 2/1999 |
| CN | 1309175 | * 8/2001 |
| EP | 0041373 | 12/1981 |
| EP | 553377 | 8/1993 |
| EP | 1375652 | 1/2004 |
| ES | 475500 | 4/1979 |
| FR | 2222433 | 10/1974 |
| GB | 1397873 | * 6/1975 |
| JP | 60028893 | 2/1985 |
| SU | 1071637 | 2/1974 |
| SU | 415983 A | 11/1974 |
| SU | 1722364 | 3/1992 |
| SU | 1750570 | 7/1992 |
| WO | WO87/02705 | 5/1987 |
| WO | WO95/04814 | 2/1995 |
| WO | WO99/60142 | 11/1999 |
| WO | WO 02/20431 | 3/2002 |
| WO | WO 02/62981 | 8/2002 |
| WO | WO 02/62982 | 8/2002 |
| WO | WO 02/62983 | 8/2002 |
| WO | WO 02/62984 | 8/2002 |
| WO | WO 02/62985 | 8/2002 |
| WO | WO 02/070682 A2 | 9/2002 |
| WO | WO02070436 | 9/2002 |
| WO | WO02070683 | 9/2002 |
| WO | WO2004108919 | 12/2004 |

OTHER PUBLICATIONS

Bassett, C.A.L. et al., "Beneficial Effects of Electromagnetic Fields", *Journal of Cellular Biochemistry*, 51, pp. 387-393 (1993).

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83-89 (1997).

Conti, P. et al., "Effect of Electromagnetic Fields on Several CD Markers and Transcription and Expression of CD4", *Immunobiology*, 201, pp. 36-48 (1999).

Deguchi, T. et al., "Nylon biodegradation by lignin-degarding fungi", *Applied and Environmental Microbiology*, 63(1): 329-331 (1997).

Dufresne C. et al., "Tea, Kombucha, and Health: A review," *Food Research International*, 33:409-421 (2000).

Gonzalez, A.M. et al., "Effects of an Electric Field of Sinusoidal Waves on the Amino Acid Biosynthesis by Azotobacter", *Z. Naturforsch*, 35, pp. 258-261 (1980).

Goodman, E.M. et al., "Effects of Electromagnetic Fields on Molecules and Cells", *International Review of Cytology*, 158, pp. 279-339 (1995).

Greenwalt C.J. et al., "Kombucha, the fermented tea: Microbiology, composition, and claimed health effects," *Journal of Food Protection*, 63:976-981 (2000).

Grospietsch, T. et al., "Stimulating Effects of Modulated 150 MHz Electromagnetic Fields on the Growth of *Escherichia coli* in a Cavity Resonator", *Bioelectrochemistry and Bioenergetics*, 37, pp. 17-23 (1995).

Grundler W. et al., "Resonant-like dependence at yeast growth rate on microwave frequencies," *The British Journal of Cancer*, Supplement, England Mar. 1982, 45:206-208 (1982).

Grundler, W. et al., "Mechanisms of Electromagnetic Interaction with Cellular Systems", *Naturwissenschaften*, 79, pp. 551-559 (1992).

Grundler, W. et al., "Nonthermal Effects of Millimeter Microwaves on Yeast Growth", *Z. Naturforsch*, 33, pp. 15-22 (1978).

Ivaschuk, O.I. et al., "Exposure of Nerve Growth Factor-Treated PC12 Rat Pheochromocytoma Cells to a Modulated Radiofrequency Field at 836.55 MHz: Effects on c-*jun* and c-*fos* Expression", *Bioelectromagnetics*, 18, pp. 223-229 (1997).

Jelinek, F. et al., "Microelectronic Sensors for Measurement of Electromagnetic Fields of Living Cells and Experimental Results", *Bioelectrochemistry and Bioenergetics*, 48, pp. 261-266 (1999).

Lacy-Hulbert, A. et al., "Biological Responses to Electromagnetic Fields", *FASEB Journal*, 12, pp. 395-420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91-96 (1994).

Lin, H. et al., "Magnetic Field Activation of Protein-DNA Binding", *Journal of Cellular Biochemistry*, 70, pp. 297-303 (1998).

Lin, H. et al., "Specific Region of the c-*myc* Promoter Is Responsive to Electric and Magnetic Fields", *Journal of Cellular Biochemistry*, 54, pp. 281-288 (1994).

Liu C.H. et al., "The Isolation and indentification of microbes from a fermented tea beverage, Haipao, and their interactions during Haipao fermentation," *Food Microbiology* (London), 13:407-415 (1996).

Loberg, L.I. et al., "Expression of Cancer-Related Genes in Human Cells Exposed to 60 Hz Magnetic Fields", *Radiation Research*, 153, pp. 679-684 (2000).

Mayser P. et al., "The yeast spectrum of the 'tea fungus Kombucha'," *Mycoses*, Blackwell, Berlin, Germany, 38:289-295 (1995).

Moore, R.L., "Biological Effects of Magnetic Fields: Studies with Microorganisms", *Canadian Journal of Microbiology*, 25, pp. 1145-1151 (1979).

Morehouse, C.A. et al., "Exposure of Daudi Cells to Low-Frequency Magnetic Fields Does Not Elevate MYC Steady-State mRNA Levels", *Radiation Research*, 153, pp. 663-669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879-880 (1997).

Novelli, G. et al., "Study of the Effects on DNA of Electromagnetic Fields Using Clamped Homogeneous Electric Field Gel Electrophoresis", *Biomedicine & Pharmacotherapy*, 45, pp. 451-454 (1991).

Phillips, J.L., "Effects of Electromagnetic Field Exposure on Gene Transcription", *Journal of Cellular Biochemistry*, 51, pp. 381-386 (1993).

Pichko, V. B. et al., "Electromagnetic stimulation of productivity of microorganisms and its mechanisms", *Prikladnaya Biokhimiya I Mikrobiologiya*, 32(4): 468-472 (1996).

Ponne, C. T. et al., "Interaction of electromagnetic energy with biological material-relation to food processing", *Radiation Physics and Chemistry*, 45(4): 591-607 (1995).

Romano-Spica, V. et al., "Ets1 Oncogene Induction by ELF-Modulated 50 MHz Radiofrequency Electromagnetic Field", *Bioelectromagnetics*, 21, pp. 8-18 (2000).

Surawicz Christina M. et al., "The search for a better treatment for recurrent Clostridium difficile disease: Use of high-dose vancomycin combined with *Saccharomyces boulardii*," *Clinical Infectious Diseases*, 31:1012-1017 (2000).

Trosko, J.E., "Human Health Consequences of Environmentally-Modulated Gene Expression: Potential Roles of ELF-EMF Induced Epigenetic Versus Mutagenic Mechanisms of Disease", *Bioelectromagnetics*, 21, pp. 402-406 (2000).

Van den Bogaerde J. et al., "Immune sensitization to food, yeast and bacteria In Crohn's disease," *Alimentary Pharmacology & Therapeutics*, 15:1647-1653 (2001).

Van Rensburg, P. et al., "Engineering yeast for efficient cellulose degradation", *Yeast*, 14(1): 67-76 (1998).

Ventura, C. et al., "Elf-pulsed Magnetic Fields Modulate Opioid Peptide Gene Expresssion in Myocardial Cells", *Cardiovascular Research*, 45, pp. 1054-1064 (2000).

Woodward, A.M. et al., "Genetic Programming as an Analytical Tool for Non-linear Dielectric Spectroscopy", *Bioelectrochemistry and Bioenergetics*, 48, pp. 389-396 (1999).

Yonetani, T. et al., "Electromagnetic Properties of Hemoproteins", *The Journal of Biological Chemistry*, 247, pp. 2447-2455 (1972).

Zhang, L. et al., "Electrostimulation of the Dehydrogenase System of Yeast by Alternating Currents", *Bioelectrochemistry and Bioenergetics*, 28, pp. 341-353 (1992).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

U.S. Appl. No. 10/192,805, filed Nov. 29, 2004, Zhang.

U.S. Appl. No. 10/192,807, filed Nov. 29, 2004, Cheung.

Born et al., "The *Saccharomyces boulardii* Therapy of HIV-Associated Diarrhea", *Deutsche Medizinische Wochenschrift*, 118(20):765 (1993). (in German with English translation).

Dutta et al., *J. of Microwave Power*, vol. 14, No. 3, pp. 275-280 (1979).

Goodman, et al., "Magnetic Field Stress Induces Expression of HSP70", *Cell Stress & Chaperones* 3(2):79-88 (1998).

Grundler W., "Resonant Microwave Effect on Locally Fixed Yeast Microcolonies" *Z, Naturforsch* 44c:863-866 (1989).

Kim et al., "Anti-Stress and Anti-Fatigue Effects of Fermented Rice Bran", *Biosci Biotechnol Biochem.*, 65(10):2294-6 (2001).

Lin H. et al., "A Magnetic Field-Responsive Domain in the Human HSP70 Promoter", *J Cell Biochem*, 75:170-176 (1999).

Machado Caetano et al., "Immunopharmacological Effects of *Sacchoramyces boulardii* in Healthy Human Volunteers", *Int'l Immunology and Immunopathology*, 8(3):245-259 (1986).

Ortuno et al., "Oral Administration of Yeast, *Saccharomyces cerevisiae*, Enhances the Cellular Innate Immune response to Gilthead Seabream (*Sparus aurata L.*)", *Vet Immunol Immunopathol*, 85(1-2):41-50 (2002).

Peret Filho et al., "Dose Effect of Oral *Saccharomyces boulardii* Treatments on Morbidity and Mortality in Immunosuppressed Mice", *J Med Microbiol.*, 47(2):111-6 (1998).

Saha et al., "Microbial Manipulation of Rumen Fermentation Using *Saccharomyces cerevisiae* as Probiotics", *Current Science* (Bangalore), 77(5):696-697 (1999).

WHO World Health Organization; WebPages http:www.who.int/peh-emf/about/WhatisEMF/en/ and http:www.who.int/peh-emf/about/WhatisEMF/en/index3.html retrieved Jun. 10, 2004.

* cited by examiner

METHODS AND COMPOSITIONS FOR TREATING EPILEPSY

FIELD OF THE INVENTION

The invention relates to compositions that treat epilepsy and can be taken as dietary supplements or medication. These compositions contain yeast cells obtainable by growth in electromagnetic fields with specific frequencies and field strengths.

BACKGROUND OF THE INVENTION

Epilepsy is a chronic illness caused by abnormality in the central nervous system. An epileptic seizure is a brief, excessive surge of electrical activity in the brain that causes a change in consciousness, sensation and behavior. During an epileptic seizure, the regulatory systems that maintain the normal balance between excitation and inhibition of the brain's electrical activity break down. There may be a loss of inhibitory nerve cells or an overproduction of an excitatory neurotransmitter. Groups of abnormal cells are activated synchronously, creating a storm of electrical activity.

Patients taking anticonvulsant drugs display a broad spectrum of side-effects. The widely used drug carbamazepine, shows side effects such as dizziness, ataxia, drowsiness and reduction of alertness. See, A. Delcker et al., *Eur. Neuropsychopharmacold.*, 7, pp. 213-8 (1997). Valproic acid may precipitate metabolic disorders, liver disease, gastrointestinal symptomatology, excessive bodyweight gain and alopecia. See, S. J. Wallace, *Drug Saf*, 15, pp. 378-93 (1996). Barbiturates precipitates metabolic bone disease and rash. See, S. J. Wallace, *Drug Saf*, 15, pp. 378-93 (1996). Therefore, there is a need on the market for anticonvulsant medication with fewer side effects.

SUMMARY OF THE INVENTION

The composition of the invention assists in the recovery of epilepsy and can be taken as dietary supplements in the form of health drinks or pills.

This invention embraces a composition comprising a plurality of yeast cells that have been cultured in the presence of an alternating electric field having a frequency in the range of about 10200 to 13040 MHz and a field strength in the range of about 20 to 600 mV/cm. In one embodiment, the frequency is in the range of about 10200-10270, 12330-12390, or 12970-13040 MHz. In another embodiment, the field strength is in the range of about 200-500 mV/cm. The yeast cells are cultured in the alternating electric field for a period of time sufficient to increase the capability of said plurality of yeast cells to have an anti-seizure effect or treat epilepsy as compared to unactivated yeast cells. In one embodiment, the composition comprising the activated yeast cells reduces the occurrence of epileptic seizures in mammals. Preferably, the mammal is human. In one embodiment, the human has seizure activity. In one embodiment, the frequency and/or the field strength of the alternating electric field can be altered within the aforementioned ranges during said period of time. In other words, the yeast cells can be exposed to a series of electromagnetic fields. An exemplary period of time is about 140-210 hours.

Also included in this invention is a composition comprising a plurality of yeast cells that have been cultured under acidic conditions in an alternating electric field having a frequency in the range of about 12970-13040 MHz and a field strength in the range of about 260 to 510 mV/cm (e.g., 260-280, 330-360, 350-380, 430-470 or 470-510 mV/cm). In one embodiment, the yeast cells are exposed to a series of electromagnetic fields. An exemplary period of time is about 180-210 hours.

Included in this invention are also methods of making the above compositions and methods of treating a subject with epilepsy.

Yeast cells that can be included in this composition can all be derived from parent strains publically available from the China General Microbiological Culture Collection Center ("CGMCC") (China Committee for Culture Collection of Microorganisms, Institute of Microbiology, Chinese Academy of Sciences, Haidian, P.O. BOX 2714, Beijing, 100080, China). Useful yeast species include, but are not limited to *Schizosaccharomyces pombe, Saccharomyces sake, Saccharomyces uvarum, Saccharomyces rouxii, Saccharomyces carlsbergensis, Rhodotorula aurantiaca* and *Saccharomyces cerevisiae*. In one embodiment, the yeast species is *Saccharomyces carlsbergensis* Hansen or *Saccharomyces cerevisiae* Hansen. For instance, the yeast cells can be of the strain *Saccharomyces cerevisiae* Hansen IFFI1335. In one embodiment, the yeast cells are from the strains selected from the group consisting of *Saccharomyces cerevisiae* Hansen AS2.501, AS2.502, AS2.503, AS2.504, AS2.535, AS2.558, AS2.560, AS2.561, AS2.443 and AS2.562. Other useful yeast species are illustrated in Table 1.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
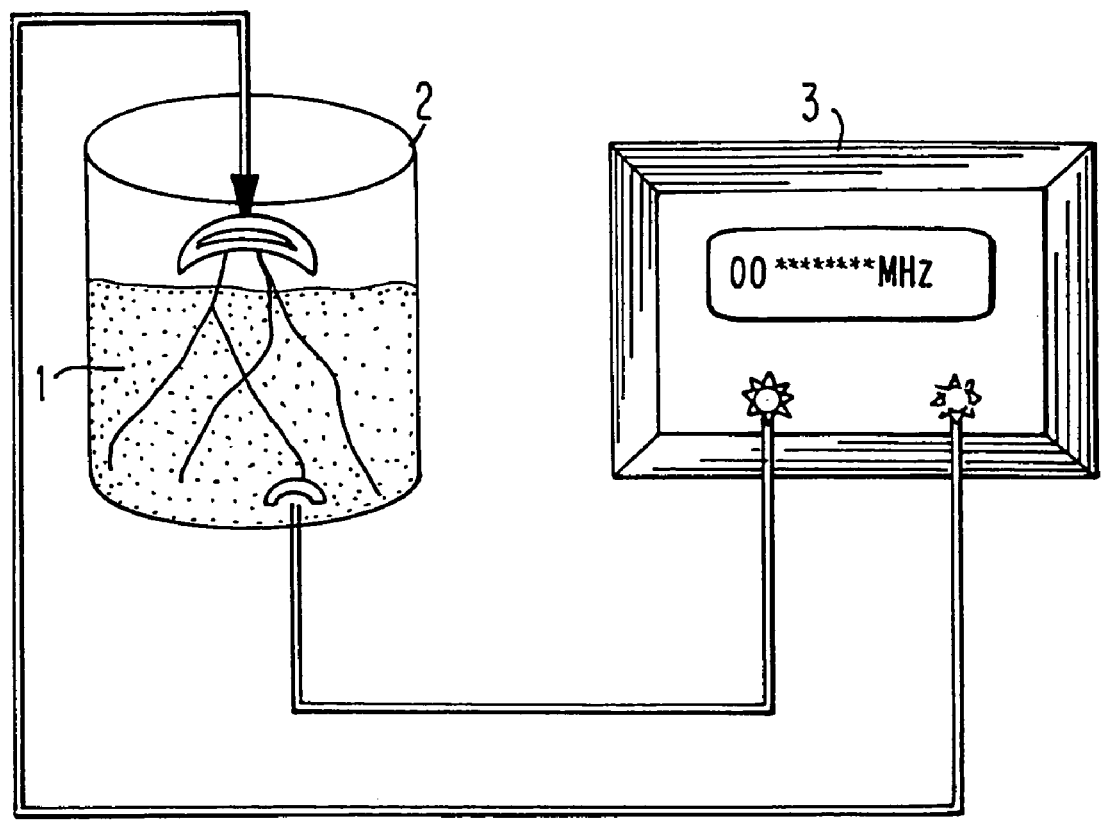
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in treating epilepsy. Yeast compositions comprising activated yeast cells can be used as medication or dietary supplements in the form of health drinks or dietary pills. In one embodiment, the yeast compositions of this invention have an anti-seizure effect in a mammal. In one embodiment, the mammal is human.

Since the activated yeast cells contained in these yeast compositions have been cultured to endure acidic conditions of pH 2.5-4.2, the compositions are stable in the stomach and can pass on to the intestines. Once in the intestines, the yeast cells are ruptured by various digestive enzymes, and agents for regulating the central nervous system are released and readily absorbed.

I. Yeast Strains Useful in the Invention

The types of yeasts useful in this invention include, but are not limited to, yeasts of the genera *Saccharomyces, Schizosaccharomyces*, and *Rhodotorula*.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are illustrated in Table 1. In general, yeast strains preferred in this invention are those used for fermentation in the food and wine industries. As a result, compositions containing these yeast cells are safe for human consumption.

The preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| | | | | |
|---|---|---|---|---|
| ACCC2034 | ACCC2035 | ACCC2036 | ACCC2037 | ACCC2038 |
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| | | | | |
|---|---|---|---|---|
| ACCC2043 | AS2.2 | AS2.3 | AS2.8 | AS2.53 |
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| | |
|---|---|
| AS2.131 | AS2.213 |

*Saccharomyces delbrueckii*

| |
|---|
| AS2.285 |

*Saccharomyces delbrueckii* Lindner ver. *mongolicus* (Saito) Lodder et van Rij

| | |
|---|---|
| AS2.209 | AS2.1157 |

*Saccharomyces exiguous* Hansen

| | |
|---|---|
| AS2.349 | AS2.1158 |

*Saccharomyces fermentati* (Saito) Lodder et van Rij

| | |
|---|---|
| AS2.286 | AS2.343 |

TABLE 1-continued

Exemplary Yeast Strains

*Saccharomyces logos* van laer et Denamur ex Jorgensen

AS2.156    AS2.327    AS2.335

*Saccharomyces mellis* (Fabian et Quinet) Lodder et kreger van Rij

AS2.195

*Saccharomyces mellis* Microellipsoides Osterwalder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

AS2.178    AS2.180    AS2.370    AS2.371

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

AS2.1207    AS2.1216    AS2.1220    AS2.1379    AS2.1398
AS2.1399    AS2.1400

*Candida parapsilosis* (Ashford) Langeron et Talice Var. intermedia Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

AS2.511     AS2.1367    AS2.1369    AS2.1372    AS2.1373
AS2.1377    AS2.1378    AS2.1384

*Candida tropicalis* (Castellani) Berkhout

ACCC2004    ACCC2005    ACCC2006    AS2.164    AS2.402
AS2.564     AS2.565     AS2.567     AS2.568    AS2.617
AS2.637     AS2.1387    AS2.1397

*Candida utilis* Henneberg Lodder et Kreger Van Rij

AS2.120    AS2.281    AS2.1180

*Crebrothecium ashbyii* (Guilliermond)
Routein (*Eremothecium ashbyii* Guilliermond)

AS2.481    AS2.482    AS2.1197

*Geotrichum candidum* Link

ACCC2016    AS2.361     AS2.498     AS2.616    AS2.1035
AS2.1062    AS2.1080    AS2.1132    AS2.1175   AS2.1183

*Hansenula anomala* (Hansen)H et P sydow

ACCC2018   AS2.294    AS2.295    AS2.296    AS2.297
AS2.298    AS2.299    AS2.300    AS2.302    AS2.338
AS2.339    AS2.340    AS2.341    AS2.470    AS2.592
AS2.641    AS2.642    AS2.782    AS2.635    AS2.794

*Hansenula arabitolgens* Fang

AS2.887

*Hansenula jadinii* (A. et R Sartory Weill et Meyer) Wickerham

ACCC2019

TABLE 1-continued

Exemplary Yeast Strains

*Hansenula saturnus* (Klocker) H et P sydow

ACCC2020

*Hansenula schneggii* (Weber) Dekker

AS2.304

*Hansenula subpelliculosa* Bedford

| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| ACCC2022 | ACCC2023 | AS2.197 | AS2.496 | AS2.714 |
| ACCC2021 | AS2.711 | | | |

*Lipomycess starkeyi* Lodder et van Rij

AS2.1390   ACCC2024

*Pichia farinosa* (Lindner) Hansen

| ACCC2025 | ACCC2026 | AS2.86 | AS2.87 | AS2.705 |
| AS2.803 | | | | |

*Pichia membranaefaciens* Hansen

ACCC2027   AS2.89   AS2.661   AS2.1039

*Rhodosporidium toruloides* Banno

ACCC2028

*Rhodotorula glutinis* (Fresenius) Harrison

| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| AS2.102 | AS2.107 | AS2.278 | AS2.499 | AS2.694 |
| AS2.703 | AS2.1146 | | | |

*Saccharomyces carlsbergensis* Hansen

| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| IFFI1023 | IFFI1032 | IFFI1036 | IFFI1044 | IFFI1072 |
| IFFI1205 | IFFI1207 | | | |

*Saccharomyces willianus* Saccardo

| AS2.5 AS2.7 | AS2.119 | AS2.152 | AS2.293 | |
| AS2.381 | AS2.392 | AS2.434 | AS2.614 | AS2.1189 |

*Saccharomyces* sp.

AS2.311

*Saccharomycodes ludwigii* Hansen

ACCC2044   AS2.243   AS2.508

*Saccharomycodes sinenses* Yue

AS2.1395

*Schizosaccharomyces octosporus* Beijerinck

ACCC2046   AS2.1148

*Schizosaccharomyces pombe* Lindner

| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

TABLE 1-continued

Exemplary Yeast Strains

*Sporobolomyces roseus* Kluyver et van Niel

| | | | | |
|---|---|---|---|---|
| ACCC2049 | ACCC2050 | AS2.19 | AS2.962 | AS2.1036 |
| ACCC2051 | AS2.261 | AS2.262 | | |

*Torulopsis candida* (Saito) Lodder

| | |
|---|---|
| AS2.270 | ACCC2052 |

*Torulopsis famta* (Harrison) Lodder et van Rij

| | |
|---|---|
| ACCC2053 | AS2.685 |

*Torulopsis globosa* (Olson et Hammer) Lodder et van Rij

| | |
|---|---|
| ACCC2054 | AS2.202 |

*Torulopsis inconspicua* Lodder et Kreger van Rij

AS2.75

*Trichosporon behrendii* Lodder et Kreger van Rij

| | |
|---|---|
| ACCC2056 | AS2.1193 |

*Trichosporon capitatum* Diddens et Lodder

| | |
|---|---|
| ACCC2056 | AS2.1385 |

*Trichosporon cutaneum* (de Beurm et al.) Ota

| | | | | |
|---|---|---|---|---|
| ACCC2057 | AS2.25 | AS2.570 | AS2.571 | AS2.1374 |

*Wickerhamia fluorescens* (Soneda) Soneda

| | |
|---|---|
| ACCC2058 | AS2.1388 |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 10200 to 13040 (e.g., 10200 to 10270, 12330 to 12390 and 12970 to 13040 MHz). Exemplary frequencies include 10231, 10237, 12361, 12997 and 13008 MHz. The field strength of the electric field useful in this invention ranges from about 20 to 600 mV/cm (e.g., 240-300, 310-340, 350-380, 380-430, 430-470 and 470-510 mV/cm). Exemplary field strengths include 246, 272, 288, 322, 343, 346, 364, 393, 446 and 483 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9, 10, 11, 12, 13 or more EMFs in a series. In one embodiment, the yeast culture is exposed to a series of EMFs, wherein the frequency of the electric field is alternated in the range of about 10200 to 10270, 12330 to 12390 and 12970 to 13040 MHz.

Although the yeast cells can be activated after even a few hours of culturing in the presence of an EMF, it may be preferred that the compositions comprising activated yeast cells be allowed to multiply and grow in the presence of the EMF(s) for a total of about 140-210 hours. In the presence of 13 EMFs, the compositions can be grown for about 50-380, 80-380, 100-350, or 250-350 hours. In the presence of 1 EMF, the compositions can be grown for about 5-60, 10-50, 80-180 or 100-150 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 30 GHz.

The alternating electric field can be applied to the culture by a variety of means, including placing the yeast culture (1)

in close proximity to the signal emitters such as a metal wire or tube capable of transmitting EMFs. The metal wire or tube can be made of red copper, and be placed inside the container (2), reaching as deep as 3-30 cm. For example, if the fluid in the container (2) has a depth of 15-20 cm, 20-30 cm, 30-50 cm, 50-70 cm, 70-100 cm, 100-150 cm or 150-200 cm, the metal wire can be 3-5 cm, 5-7 cm, 7-10 cm, 10-15 cm, 15-20 cm, 20-30 cm and 25-30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10-100 L, metal wires/tubes having a diameter of 3 to 5 mm can be used. For a culture having a volume of 100-1000 L, metal wires/tubes having a diameter of 6 to 15 mm can be used. For a culture having a volume greater than 1000 L, metal wires/tubes having a diameter of 20-25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients assimilatable by yeast cells. Complex carbon-containing substances in a suitable form (e.g., carbohydrates such as sucrose, glucose, dextrose, maltose, starch and xylosel; or mannitol) can be the carbon sources for yeast cells. The exact quantity of the carbon sources can be adjusted in accordance with the other ingredients of the medium. In general, the amount of carbon-containing substances varies between about 0.5% and 10% by weight of the medium, and preferably between about 1% and 5%, most preferably between about 1.0-2.0%. Vitamins can also be added to the medium, for example, Vitamin E, $D_3$, H and $B_6$. Among the inorganic salts which can be added to a laboratory culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, $NaCl$, and $CaSO_4$.

IV. Electromagnetic Activation of Yeast Cells

To activate or enhance the innate ability of yeast cells to produce agents that are useful in regulating the central nervous system, these cells can be cultured in an appropriate medium under sterile conditions at 20° C.-35° C. (e.g., 28-32° C.) for a sufficient amount of time, e.g. 5-60, 10-50, 80-180, 100-150, 140-210, 50-380, 80-380, 100-350, or 250-350 hours in an alternating electric field or a series of alternating electric fields as described above.

An exemplary set-up of the culture process is depicted in FIG. 1 (see above). An exemplary culture medium contains the following in per 1000 ml of sterile water: 6.0 g of sucrose, 12 g of mannitol, 60 μg of Vitamin E, 50 μg of Vitamin $D_3$, 60 μg Vitamin H, 90 μg of Vitamin $B_6$, 50 ml bovine serum, 0.2 g of $KH_2PO_4$, 0.25 g of $MgSO_4 \cdot 7H_2O$, 0.3 g of NaCl, 0.2 g of $CaSO_4 \cdot 2H_2O$, 4.0 g of $CaCO_3 \cdot 5H_2O$ and 2.5 g of peptone. All vitamins are sterilized before added to the solution. Yeast cells of the desired strains are then added to the culture medium to form a mixture containing $1 \times 10^8$ yeast cells per 1000 ml of culture medium. The yeast cells can be of any of the strains illustrated in Table 1. In one embodiment, the yeast cells are of the strain *Saccharomyces cerevisiae* Hansen IFFI1335. The mixture is then added to the apparatus of FIG. 1.

The activation process of the yeast cells involves the following steps: 1) maintaining the temperature of the activation apparatus at 20-35° C. (e.g., 28-32° C.), and culturing the yeast cells for 28 hours; 2) applying an electric field having a frequency of about 10231 MHz and a field strength of 240-260 mV/cm (e.g., about 246 mV/cm) for 16 hours; 3) then applying an electric field having a frequency of about 10237 MHz and a field strength of 310-340 mV/cm (e.g., about 322 mV/cm) for 42 hours; 4) then applying an electric field having a frequency of about 12361 MHz and a field strength of 350-380 mV/cm (about 364 mV/cm) for 38 hours; 5) then applying an electric field having a frequency of about 12997 MHz and a field strength of 380-420 mV/cm (e.g., about 393 mV/cm) for 38 hours; 6) then applying an electric field having a frequency of about 13008 MHz and a field strength of 280-300 mV/cm (e.g., about 288 mV/cm) for 16 hours; and 7) finally lyophilizing the activated yeast cells to form a powder and storing the powder at 4° C. Preferably, the concentration of the lyophilized yeast cells is more than $10^{10}$ cells/g.

V. Acclimatization of Yeast Cells To the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeasts in the acidic gastric environment.

To achieve this, the yeast powder containing activated yeast cells can be mixed with an acclimatizing culture medium at 10 g (containing more than $10^{10}$ activated cells per gram) per 1000 ml. The yeast mixture is then cultured first in the presence of an alternating electric field having a frequency of about 12997 MHz and a field strength of 370-430 mV/cm (e.g., about 446 mV/cm) at about 28 to 32° C. for 34-42 hours (e.g., 38 hours). The resultant yeast cells are further incubated in the presence of an alternating electric field having a frequency of about 13008 MHz and a field strength of 350-380 mV/cm (e.g., about 364 mV/cm) at about 28 to 32° C. for 16-28 hours (e.g., 20 hours). The resulting acclimatized yeast cells are then dried and stored either in powder form ($\geq 10^{10}$ cells/g) at room temperature or stored in vacuum at 0-4° C.

An exemplary acclimatizing culture medium is made by mixing 700 ml of fresh pig gastric juice and 300 ml of wild Chinese hawthorn extract. The pH of acclimatizing culture medium is adjusted to 2.5 with 0.1 M hydrochloric acid and 0.2 M potassium biphthalate ($C_6H_4(COOK)COOH$). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. To prepare the wild Chinese hawthorn extract, 500 g of fresh wild Chinese hawthorn is dried under sterile conditions to reduce the water content ($\leq 8\%$). The dried fruit is then ground ($\geq 20$ mesh) and added to 1500 ml of sterile water. The mixture is allowed to stand for 6 hours at 4° C. under sterile conditions. The supernatant is collected to be used in the acclimatizing culture medium.

VI. Manufacture of Yeast Compositions

Figure 2:
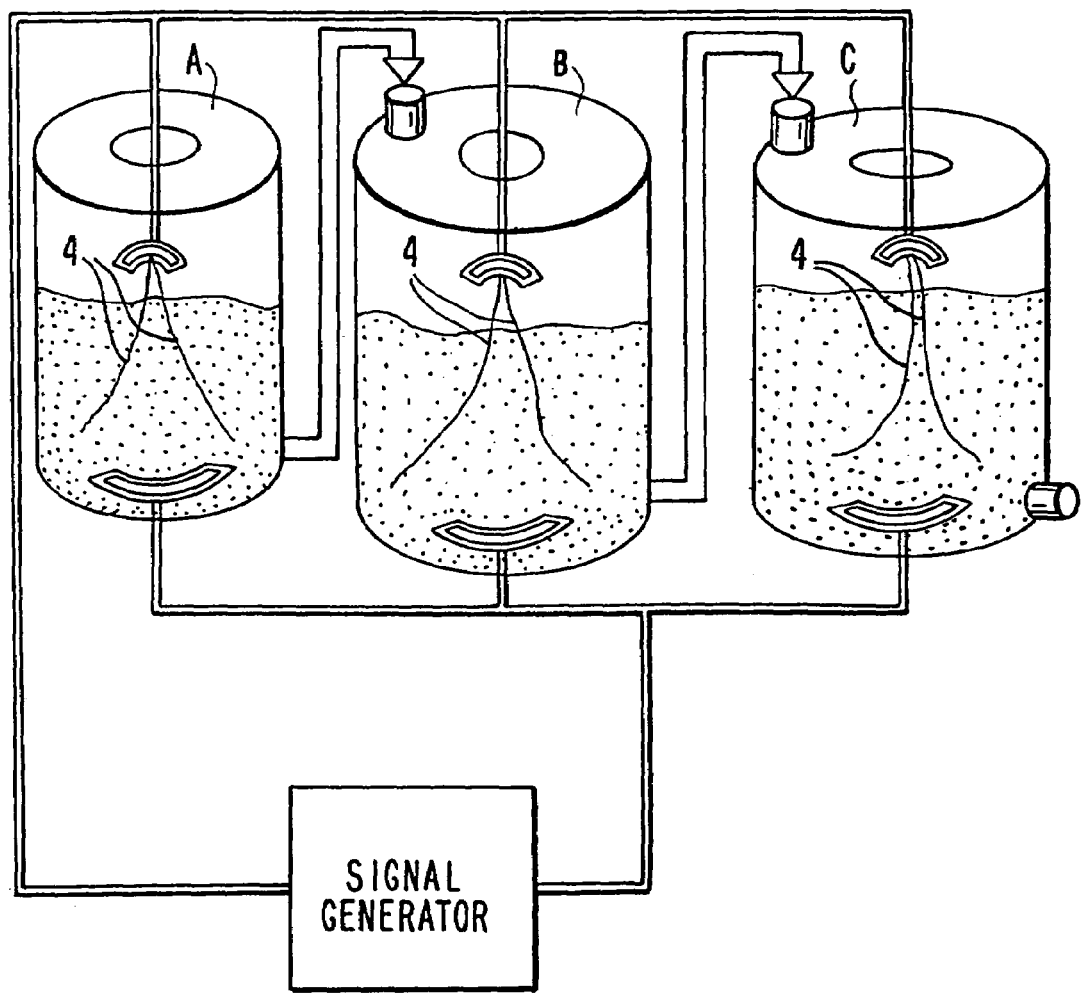
FIG. 2 is a schematic diagram showing an exemplary apparatus for making yeast compositions of the invention. The apparatus comprises a signal generator (such as models 83721B and 83741A manufactured by HP) and interconnected containers A, B and C.

To prepare the yeast compositions of the invention, an apparatus depicted in FIG. 2 or an equivalent thereof can be used. This apparatus includes a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of fruit extract from *Schisandra chinensis Baill* (wu wei zi), and 100 L of soy bean extracts. To prepare hawthorn, jujube and wu wei zi extracts, the fresh fruits are washed and dried under sterile conditions to reduce the water content to no higher than 8%. One hundred kilograms of the dried fruits are then ground ($\geq$20 mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. Once the mixed fruit extract solution is prepared, the solution is sterilized at 121° C. for 30 minutes, and cooled to 40° C. before use.

One thousand grams of the activated yeast powder prepared as described above (Section V, supra) is added to 1000 L of the mixed fruit extract solution, and the yeast solution is transferred to container (A) shown in FIG. 2. The yeast cells are then cultured in the presence of an alternating electric field having a frequency of about 12997 MHz and a field strength of about 430-470 mV/cm (e.g., about 446 mV/cm) at 28-32° C. under sterile conditions for 38 hours. The yeast cells are further incubated in an alternating electric field having a frequency of about 13008 MHz and a field strength of 330-360 mV/cm (e.g., about 343 mV/cm). The culturing continues for another 12 hours.

The yeast culture is then transferred from the first container (A) to the second container (B) (if need be, a new batch of yeast culture can be started in the now available first container (A)), and subjected to an alternating electric field having a frequency of about 12997 MHz and a field strength of 470-510 mV/cm (e.g., about 483 mV/cm) for 24 hours. Subsequently the frequency and field strength of the electric field are changed to about 13008 MHz and 350-380 mV/cm (e.g., about 368 mV/cm), respectively. The culturing continues for another 12 hours.

The yeast culture is then transferred from the second container (B) to the third container (C), and subjected to an alternating electric field having a frequency of about 12997 MHz and a field strength of 330-360 mV/cm (e.g., about 346 mV/cm) for 28 hours. Subsequently the frequency and field strength of the electric field are changed to about 13008 MHz and 260-280 mV/cm (e.g., about 272 mV/cm), respectively. The culturing continues for another 12 hours.

The yeast culture from the third container (C) can then be packaged into vacuum sealed bottles of 30-50 ml or 100 ml for use as a dietary supplement, e.g., health drinks, or medication in the form of pills, powder, etc. The dietary supplement can be taken 3-4 times daily at 30-60 ml each time for a period of three months (10-30 minutes before meals and at bedtime). If desired, the final yeast culture can also be dried within 24 hours and stored in powder form.

In one embodiment, the compositions of the invention can also be administered intravenously or peritoneally in the form of a sterile injectable preparation. Such a sterile preparation is prepared as follows. A sterilized health drink composition is first treated under ultrasound (>=18,000 Hz) for 10 minutes and then centrifuged at 4355 rpm for another 10 minutes. The resulting supernatant is adjusted to pH 7.2-7.4 using 1 M NaOH and subsequently filtered through a membrane (0.22 µm for intravenous injection and 0.45 µm for peritoneal injection) under sterile conditions. The resulting sterile preparation is submerged in a 35-38° C. water bath for 30 minutes before use.

The yeast compositions of the present invention are derived from yeasts used in food and pharmaceutical industries. The yeast compositions are thus devoid of side effects associated with many pharmaceutical compounds.

In other embodiments, the compositions of the invention may also be formulated with pharmaceutically acceptable carriers to be orally administered in any orally acceptable dosage form including, but not limited to, capsules, tablets, suspensions or solutions.

EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen IFFI1335 cultured in the presence of an alternating electric field having the electric field frequency and field strength exemplified in the parentheses following the recommended ranges in Section IV, supra. Control yeast compositions were those prepared in the same manner except that the yeast cells were cultured in the absence of EMFs. Unless otherwise indicated, the yeast compositions and the corresponding controls were admitted to the animals via intragastric feeding.

Example 1

Anti-seizure Effect on Electroshocked Mice

Electrodes are placed at the ears of the mice to provide instant stimulation through a strong electric currency. An appropriate electric currency induces an excessive surge of electrical activity in the brain resulting in seizures to occur.

Kunming grade healthy mice, which were 50-70 days old, weighing 18-22 g, were provided by the Institute of Zoology, Chinese Academy of Sciences, Beijing, China. The electroshock device (model GJ-2, manufactured by Medical Instrument Factory, Zhejiang Medical University) was adjusted to an output frequency of 60 Hz and voltage of 125 V. An equal number of male and female mice were selected. The ears of the mice were covered with saturated saline soaked-cotton. The electrodes were then clipped onto the ears of the mice. The mice were electroshocked three times for 0.3 seconds at an interval of 10 seconds. Mice with seizure activity were then divided into four groups, each group containing 70 mice: the test group (AY), the control yeast group (NY), the positive control group (CK2) and negative control group (CK1). Each mouse in the test, control yeast and negative control groups was administered twice daily 0.4 ml of the activated yeast composition, the control yeast composition, and saline, respectively, for 1 week. Each mouse in the positive control group was administered twice daily 15 mg/kg of phenobarbital for 1 week.

On each day, the mice were electroshocked once for 0.3 seconds. The number of mice with seizure activity were monitored as illustrated in Table 2.

TABLE 2

| Group | Day 1 | | Day 2 | | Day 3 | | Day 4 | |
|---|---|---|---|---|---|---|---|---|
| | No. mice with seizure activity | % mice with anti-seizure | No. mice with seizure activity | % mice anti-seizure | No. mice with seizure activity | % mice anti-seizure | No. mice with seizure activity | % mice anti-seizure |
| AY | 67 | 4.3 | 56 | 20 | 44 | 37.1 | 32 | 54.3 |
| NY | 70 | 0 | 70 | 0 | 70 | 0 | 69 | 1.4 |
| CK2 | 59 | 15.7 | 48 | 31.4 | 56 | 20 | 55 | 21.4 |
| CK1 | 70 | 0 | 70 | 0 | 70 | 0 | 70 | 0 |

| Group | Day 5 | | Day 6 | | Day 7 | |
|---|---|---|---|---|---|---|
| | No. mice with seizure activity | % mice anti-seizure | No. mice with seizure activity | % mice anti-seizure | No. mice with seizure activity | % mice anti-seizure |
| AY | 17 | 75.7 | 4 | 94.3 | 1 | 98.6 |
| NY | 70 | 0 | 70 | 0 | 70 | 0 |
| CK2 | 58 | 17.1 | 61 | 12.8 | 61 | 12.9 |
| CK1 | 70 | 0 | 70 | 0 | 70 | 0 |

As illustrated above, compared to the control (CK1) and control yeast (NY) groups, the test group (AY) shows a significant decrease in the number of rats with seizure activity after day 4. Further, nearly all of the rats in the test group show an anti-seizure effect after day 7, while only 12.9% of the rats in the positive control group (CK2) have an anti-seizure effect. Thus, the activated yeast composition of this invention has an anti-seizure affect on electro-shocked mice.

Example 2

Anti-Seizure Effect of Rats Induced with Cardiazol

Cardiazol induces seizure activity through intensifying excitatory synaptic activity of the brain. At the appropriate dose, cardiazol induces epileptic bursts that occur spontaneously.

An equal number of female and male Wistar rats that were 5-6 months old, weighing 200-220 g were provided by the Chinese Academy of Military Medical Sciences, Beijing, China. The rats were divided into four groups, each containing 20 rats: the test group (AY), the control yeast group (NY), the positive control group (CK2) and negative control group (CK1). Each rat in the test, control yeast and negative control groups was administered twice daily 0.6 ml of the activated yeast composition, the control yeast composition, and saline, respectively, for 1 week. Each mouse in the positive group was administered twice daily 0.04 g/kg (body weight) of phenobarbital (dissolved in 0.6 ml saline) for 1 week.

On day 7, 30 minutes after administering the last dosage of the above compositions, each group was administered by subcutaneous injection 70 mg/kg (body weight) of cardiazol (prepared as a 5% cardiazol solution in saline). The number of seizures occurred, incubation time (time between completion of injection and first seizure) and life span after injection was recorded immediately thereafter as shown in Table 3.

TABLE 3

| Group | Animal number | incubation time (min) | life span (min) |
|---|---|---|---|
| AY | 20 | 11.82 ± 1.52 | 68.33 ± 16.26 |
| NY | 20 | 2.52 ± 1.16 | 8.23 ± 3.42 |
| CK2 | 20 | 7.23 ± 5.32 | 22.76 ± 17.37 |
| CK1 | 20 | 2.60 ± 1.21 | 7.62 ± 3.65 |

As illustrated above, compared to the control yeast (NY), negative control groups (CK1), the test group (AY) shows a significant increase in the incubation time of the seizure and the life span of the rat after cardiazol injection. Further, compared to the positive control group (CK2), the test group shows that the incubation time of the seizure as well as the life span of the rat after cardiazol injection is much higher. Thus, the activated composition of this invention has an anti-seizure effect on rats treated with a seizure-inducing drug, cardiazol.

While a number of embodiments of this invention have been set forth, it is apparent that the basic constructions may be altered to provide other embodiments which utilize the compositions and methods of this invention.

What is claimed is:

1. A method of preparing a yeast composition, comprising: culturing yeast cells of *Saccharomyces cerevisiae* Hansen IFFI1335 strain for a period of 50-380 hours in the presence of an alternating electric field having a frequency in the range of about 10200 to 13040 MHz and a field strength in the range of about 20 to 600 mV/cm.

2. The method of claim 1, wherein the range of the frequency is about 10200 to 10270, 12330 to 12390 or 12970 to 13040 MHz.

3. The method of claim 1, wherein the range of the field strength is about 200 to 500 mV/cm.

4. A method of treating epilepsy in a subject having epilepsy, comprising the step of administering to said subject the composition made by the method of any one of claims 1 to 3.

5. The method of claim 4, wherein the administration is through oral administration.

6. The method of claim 1, wherein the composition is in the form of a tablet, powder or health drink.

7. The method of claim 1, wherein the composition is in the form of a health drink.

* * * * *

UNITED STATES PATENT AND TRADEMARK OFFICE
CERTIFICATE OF CORRECTION

PATENT NO. : 7,297,522 B2
APPLICATION NO. : 10/717137
DATED : November 20, 2007
INVENTOR(S) : Ling Y. Cheung Page 1 of 1

It is certified that error appears in the above-identified patent and that said Letters Patent is hereby corrected as shown below:

Column 1, lines 27-28: "*Neuropsychopharmacold*" should read -- *Neuropsychopharmacol* --.

Column 11, line 51: "20° C.-35° C." should read -- 20°C-35°C --.

Column 11, line 62: "$CaCO_3°5H_2O$" should read -- $CaCO_3·5H_2O$ --.

Signed and Sealed this

Seventeenth Day of June, 2008

JON W. DUDAS
*Director of the United States Patent and Trademark Office*